United States Patent
Campos et al.

(10) Patent No.: US 8,268,306 B2
(45) Date of Patent: Sep. 18, 2012

(54) PESTICIDAL AND ANTIPARASITIC COMPOSITIONS

(75) Inventors: Jesus Mena Campos, Camaguey (CU); Eulogio Pimentel Vazquez, Camaguey (CU); Armando Tomas Hernadez Garcia, Camaguey (CU); Liuven Veloz Gonzalez, Camaguey (CU); Marieta Marin Bruzos, Camaguey (CU); Oscar Compte Alberto, Camaguey (CU); Marilin Domingo Puente, Camaguey (CU); Licette Leon Barreras, Camaguey (CU); Merardo Pujol Ferrero, Ciudad de la Habana (CU); Juan Diego Mencho Ponce, Camaguey (CU); Carlos Borroto Nordelo, Ciudad de la Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 0 days.

(21) Appl. No.: 12/857,194

(22) Filed: Aug. 16, 2010

(65) Prior Publication Data

US 2011/0064718 A1    Mar. 17, 2011

Related U.S. Application Data

(62) Division of application No. 10/250,561, filed as application No. PCT/CU01/00014 on Dec. 17, 2001, now abandoned.

(30) Foreign Application Priority Data

Jan. 3, 2001 (CU) ................. 2001/0004

(51) Int. Cl.
*A01N 59/02* (2006.01)
*A01P 5/00* (2006.01)
*A61K 38/47* (2006.01)
*A61P 33/00* (2006.01)

(52) U.S. Cl. .................................. 424/94.61
(58) Field of Classification Search ............... 424/94.61
See application file for complete search history.

(56) References Cited

U.S. PATENT DOCUMENTS

| 4,940,840 A | 7/1990 | Suslow et al. |
| 5,208,159 A | 5/1993 | Toda et al. |
| 5,346,698 A | 9/1994 | Abercrombie |

FOREIGN PATENT DOCUMENTS

| EP | 0401560 | 12/1990 |
| WO | W09413784 | 6/1994 |
| WO | WO 9634529 | 11/1996 |

OTHER PUBLICATIONS

Khashe et al., "Biochemical and Pathogenic Properties of Shewanella alga and Shawanella putrefaciens," Journal of Clinical Microbiology, Mar. 1998, p. 783-787, vol. 36, No. 3.
Chet et al., "Biological Control of Fungal Pathogens," Applied Biochemistry and Biotechnology 1994, 48:37-43.
Hollis, et al., "Rapid Kill of Nematodes in Flooded Soil," Phytopathology Nov. 1966, 56:1015-1019.
Lamberth, "Sulfur Chemistry in Crop Protection," J. Sulfur Chemistry 2004, 25(1):39-62.
Oka et al., "New Strategies for the Control of Plant-Parasitic Nematodes," Pest Management Science 2000, 56:983-988.
Rodriguez-Kabana, "Control Biologico De Nematodos Parasitos De Plantas," Nematropica 1991, 21(1):111-122.
Spiegel et al., "Evaluation of a Newly Isolated Bacterium, *Pseudomonas chitinolytica* sp. nov., for Controlling the Root-knot Nematode Meloidogyne javanica," Biocontrol Science and Technology 1991, 1:115-125.
Rodriguez-Kabana et al., "Nematodes: Biological Controlin Rice Fields: Role of Hydrogen Sulfide," Science 1965, 148:524-526.
Herrera-Estrella et al., "Chitinases in Biological Control," Chitin and Chitinases, pp. 171-184 vol. 87 (1999).
Topp et al., "Effects of Marigold (Tagetes sp.) Roots on Soil Microorganisms," Biology and Ftertility of Soils, pp. 149-154, vol. 27, No. 2 (1998).
An 1997-437454 [41] WPIX, DNC: C1997-140499, (Micorikawa et al.).

*Primary Examiner* — Sabiha Qazi
(74) *Attorney, Agent, or Firm* — Hoffman & Baron, LLP

(57) ABSTRACT

This invention relates to pesticide and antiparasitic compositions for the control of pests, diseases and parasites attacking plants and animals. The compositions include, at least one chitinolytic agent or a chitinolytic activity-inducing agent, and sulfide or a sulfide-producing agent from microorganisms or chemical compounds, wherein the chitinolytic agent or the chitinolytic activity-inducing agent and sulfur or a sulfur-producing agent obtaining from microorganisms or chemical compounds are concurrently applied at a range significantly lower than any of the above-mentioned compounds, when they are individually to attain effective control.

5 Claims, No Drawings

PESTICIDAL AND ANTIPARASITIC COMPOSITIONS

This application is a divisional of, and claims priority to U.S. application Ser. No. 10/250,561 filed October which claims priority to International Application No. PCT/CU01/00014 filed on Dec. 17, 2001. This application also asserts priority to Cuban Application No. CU 2001/0004 filed on Jan. 3, 2001.

FIELD OF THE INVENTION

This invention comprises several synergistic compositions, of the pesticide and antiparasitic kind, useful for the control of parasitic phytonematodes and zoonematodes, some diseases (fungal and bacterial), and the control of parasitic trematodes (*Fasciola hepatica*).

BACKGROUND OF THE INVENTION

Nematodes are blamed for causing the greatest damages to agriculture in tropical, subtropical and temperate regions worldwide (Nickle W. R. (Editor). 1991. Manual of Agricultural Nematology, Marcel Dekker, Inc., New York, N.Y. Pub. 1035 pp). Plantain alone has about 20% nematode-related losses of world production, representing $178 millions each year (Sasser J. N. and Freckman D. W. 1987. A world perspective on nematology: the role of the society. Vistas on nematology: a commemoration of the twenty-fifth anniversary of the Society of Nematologists/edited by Joseph A. Veech and Donald W. Dickson. p. 7-14). Plantain and banana plantations are significantly affected by *Radopholus similis*.

*Meloidogyne* spp is the most important plant parasitic nematode, for its activity causes losses between 11% and 25% of crops in almost all the tropical regions (Sasser J. N. 1979. *Root-knot nematodes*. Ed. F. Lamberti & C. E. Taylor, Academic Press, London, p 359). Consequently, there is a great need to control those parasites that were fought against with chemical nematicides in the past. Such compounds can be highly effective; however, many of them pose a great danger on the environment. In some cases the regulating authorities have limited the amount or frequency, or both in the use of such compounds, thus compromising their nematicidal effectiveness.

Nematode control still falls short. The use of chemical nematicides is restricted each day more and more, because they have highly toxic and widespread action compounds. As a result, efforts have been made to identify the effective means to eliminate the damage caused by nematodes, in favor of reducing the use of chemical pesticides. One of the approaches is the use, of biological ones with specific mode of actions and relatively safer toxicological profiles, instead of chemical nematicides. Some of the alternative nematicides include ABG-9008, a *Myrothecium verrucaria* fungus metabolite and a combination of avermectines (or related compounds, like milbecines) with fatty acids (Abercrombie K. D. 1994. Synergistic pesticidal compositions. U.S. Pat. No. 5,346,698. Mycogen Corporation. September. 13). Likewise, a method that includes concurrent administration to eliminate damages caused to plants by nematodes, the site, soil or seeds that need treatment of a) a *Myrothecium verrucaria* fungus metabolite and b) a chemical pesticide, as well as the synergistic nematicide compositions useful in this case, is claimed under patent (Warrior P., Heiman D. F. and Rehberger Linda A. 1996. Synergistic nematocidal compositions. Abbott laboratories. WO9634529, 1996 Nov. 7). Another approach is to combine spores of *Pasteuria penetrans* a nematode bacterial parasite, with organophosphorated nematicides (Nordmeyer D. 1987. Synergistic nematocidal compositions of *Pasteuria penetrans* spores and an organophosphorus nematocide. 1987. CIBA-GEIGY AG Patent AU 06057386A1. Jan. 29, 1987).

However, preparation of *P. penetrans* spores at industrial scale faces the problem that the organism is an obligated parasite; hence it must be grown in in situ nematodes, isolated from nematode infested root digests.

Chitinolytic fungi and bacteria that share the nematode's habitat, may have certain biological balance and somehow restrict nematode proliferation. Two strains of chitinolytic bacteria (Toda T. and Matsuda H. 1993. Antibacterial, antinematode and/or plant-cell activating composition, and chitinolytic microorganisms for producing the same. Toda Biosystem Laboratory, Japan. U.S. Pat. No. 5,208,159, May 4, 1993) have been claimed as antibacterial, antinematode and/or plant-cell activating composition.

There are some examples of the chitinolytic effect on nematodes. Some of the most significant are the strains of new bacteria described (Suslow T. and Jones D. G. 1994. Novel chitinase-producing bacteria and plants. DNA Plant Technology Corporation, U.S. Pat. No. 4,940,840, Jul. 10, 1990) that are created by the introduction of DNA that codifies for chitinase production, an enzyme that can degrade chitin in fungi and nematodes. The strains are useful in the production of chitinase to inhibit plant pathogens. Novel plants resistant to pathogens are described too, as the result of introduction of DNA codifying for chitinase production.

Other instances of microorganisms that reduce nematode populations that attack plants in natural conditions are described.

Rodriguez-Kabana et al. (Rodriguez-Kabana R., Jordan J. W., Hollis J. P. 1965. Nematodes: Biological control in rice fields-role of hydrogen sulfide. Science. 148: 524-26); Hollis and Rodriguez-Kabana (Hollis, J. P., y R. Rodríguez-Kábana. 1966. Rapid kill of nematodes in flooded soil. Phytopathology 56, pp 1015-19) observed correspondence among bacterium *Desulfovibrio desulfuricans*, hydrogen sulfide production and plant parasitic nematodes, whose population decreased in Louisiana's rice plantations. Sulfides are inhibitors in the electron transport breathing process of the aerobic organism, just like other metabolites produced by certain soil bacteria (Rodríguez-Kábana, R. 1991. Control biológico de nematodos parásitos de plantas. NEMATROPICA, 21(1), pp 111-22).

PAECIL™, also known as BIOACT or Nemachek, is a biological nematicide that contains a patented strain from *Paecilomyces lilacinus*, in a dry and stable spore concentration for soil and seed treatment. This fungal species is commonly found in all soils worldwide. The patented strain used as PAECIL™ active ingredient has a particular effectiveness against plant parasitic nematodes. It was originally isolated at The Philippines University, and has been developed in Australia, Macquarie University. Furthermore, it has been broadly tested for the control of several kinds of nematodes that attack major crops in Australia, The Philippines, South Africa, and others. PAECIL™ formulation is commercially available as a pesticide registered in The Philippines, under the name of BIOACT®; in South Africa, under the name of PL PLUS; and Indonesia, under the name of PAECIL™. Currently, the Australian National Registration Authority is evaluating the product as a pesticide (Holland, R. PAECIL™. 1998. http://www.ticorp.com.au/article1.htm). The abovementioned instances fail to solve all parasitic helminth problems. Therefore, the need to implement improved means for parasite control to substitute chemical pesticides and antiparasitic products still remains.

Trematodes cause considerable economic damage to animal production and human health. The diversity of the species, relative benign pathogenicity and endemism in isolated regions seem to be essential factors that effect on the lack of knowledge on trematodes. In general terms, intestinal trematodes are zoonotic and have a large number of reservoir hosts in each species.

Economically speaking, one of the most significant trematodes is *Fasciola hepatica*, the first known parasitic trematode; it affects man by inhabiting the bile conduits. Its egg is one of the largest, ovoid and operculated from helminthes, and causes digestive malfunction consisting in gastric disepsia, colon motility malfunction, liver and bile vesicle pain, fever and hepatic colic. Other signs may include cystic forms in lungs, eyes, brain, hepatic vein, and other tissues (Saleha A. 1991. Liver fluke disease (fasciolosis) epidemiology, economic impact and public health significance. Southeast Asian J. Trop. Med. Public health 22 supp 1dic. P 361-4)

Zoohelminths have become significant pests to sheep and cattle. Antihelminthic resistance is wide, particularly in populations of small ruminant parasitic nematodes.

New supplementary techniques have been developed, others are under research. Fungus, *Duddingtonia flagrans* is a predator that forms nets, produce wide wall, motionless spores: clamidospores, able to survive the passage along the intestinal tract of cattle, equines, sheep and swine (Larsen M. 1999. Biological control of helminths. *Int J Parasitol*. January; 29(1): 139-46, and Larsen, M. 2000. Prospects for controlling animal parasitic nematodes by predacious micro fungi. Parasitology, 120, S120-S121).

Works on *D. flagrans* in Denmark, France, Australia, USA, and Mexico, have confirmed the strong potential for biological control this fungus has.

Like many other important sheep producing countries, South Africa undergoes a big crisis in terms of antihelminthic resistance, especially in gastrointestinal nematodes in sheep and goat. Significant parasitic helminthes are involved in this phenomenon; however, this causes a particular problem with abomasum hematophage parasite *Haemonchus contortus*. The studies point out that over 90% of this parasite's strains from the most important sheep producing regions in South Africa, show several drug resistance degrees, in three out of the four antihelminthic groups available in the South African market. Even in areas of common grazing in Northern Province, it was detected in five herds studied in 1993 (van Wyk J. A., Bath G. F. and Malan F. S. 2000. The need for alternative methods to control nematode parasites of ruminant livestock in South Africa. World Animal Review. http://www.fao.org/ag/AGA/AGAP/FRG/FEEDback/War/contents.htm).

Resistance increase has become serious, since it has been experienced in other areas as well. A series of antihelminthic studies have been recently conducted in four Latin American countries: Argentina (Eddi, C., Caracostantogolo, J., Peya, M., Schapiro, J., Marangunich, L., Waller, P. J. & Hansen, J. W. 1996. The prevalence of anthelmintic resistance in nematode parasites of sheep in southern Latin America: Argentina. Vet. Parasitol., 62: 189-197); Brazil (Echevarria F., Borba M. F. S., Pinheiro A. C., Waller P. J. & Hansen J. W. 1996. The prevalence of anthelmintic resistance in nematode parasites of sheep in southern Latin America: Brazil. Vet. Parasitol., 62: 199-206); Paraguay (Maciel S., Giminez A. M., Gaona, C., Waller P. J. & Hansen J. W. 1996. The prevalence of anthelmintic resistance in nematode parasites of sheep in southern Latin America: Paraguay. *Vet. Parasitol.*, 62: 207-212); and Uruguay (Nari A., Salles J., Gil A., Waller P. J. & Hansen J. W. 1996. The prevalence of anthelmintic resistance in nematode parasites of sheep in southern Latin America: Uruguay. *Vet. Parasitol.*, 62: 213-222).

One of the nematodes that causes the greatest damages to cattle is *Dictyocaulus viviparous*, a parasite that comes to sexual maturity and when adult, is lodged in the lung of cattle, particularly young animals. The diseased caused is known as verminose bronchitis, or bovine Dictyocaulosis, and infestation is produced after ingesting the 3 or infesting larvae, present in the pastures. The treatment requires antihelminthics (Borgsteede F. H. M, de Leeuw W. A. & Burg W. P. J. 1988. A comparison of the efficacy of four different long-acting boluses to prevent infections with *Dictyocaulus viviparus* in calves. The Veterinary Quarterly, Vol 10, No. 3), but success is at the expense of new strains resistant to the drugs, which make further infested animal treatment harder. The high cost of these products is a restrictive factor to the countries with a large number of resources, and harmful ecological effects are produced with the use of these formulations.

The international problem of anthelmintic resistance is compounded by the fact that, while chemotherapy continues to be the cornerstone of parasite control, there seems little hope that any novel, chemically unrelated anthelmintics will be forthcoming for at least the next decade (Soll, M. D. 1997. The future of anthelmintic therapy from an industry perspective. In J. A. van Wyk & P. C. van Schalkwyk, eds. *Managing anthelmintic resistance in endoparasites*, p. 1-5. Proceedings of the 16th International Conference of the World Association for the Advancement of Veterinary Parasitology, Sun City, South Africa, 10-15 Aug. 1997).

In the case of bacteria and pathogenic fungi, there are comprehensive reports on biologicals, whose action is mainly based on antagonism and that a large amount of them are commercially available. Some of them are Conquer (*Pseudomonas fluorescens* that antagonizes *Pseudomonas tolassii*), Galltrol-A (*Agrobacterium radiobacter*, that controls *Agrobacterium tumefaciens*), Bio-Fungus (*Trichoderma* spp, that controls the following fungi: *Phytophthora, Rhizoctonia solani, Pythium* spp, *Fusarium, Verticillium*), Aspire (*Candida oleophila* I-182 that controls *Botrytis* spp. and *Penicillium* spp), etcetera.

One of the most widely active biofungicides is *Trichoderma* spp (Chet I, Inbar J. 1994 Biological control of fungal pathogens. *Appl Biochem Biotechnol;* 48(1):37-43) a fungus whose action mechanism is largely discussed, where chitinases that degrade the cellular wall of the host fungus take part. Moreover, there are experimental evidences of chitinolytic action from fungi and bacteria used as fungal disease bioregulators (Herrera-Estrella A, Chet I. 1999. Chitinases in biological control. *EXS;* 87:171-84). However, this is not the only mode of action of bacteria over phytopathogenic fungi; there are other control ways based on the production of secondary metabolites, like hydrogen cyanide, that manages to inhibit root pathogenic fungi (Blumer C. and Haas D. 2000. Mechanism, regulation, and ecological role of bacterial cyanide biosynthesis. *Arch Microbiol March;* 173(3):170-7), in the particular case of *P. fluorescens* CHAO strain.

Analyses of bacterium-bacterium interaction have shown there are three main types: antibiosis, substrate competition and parasitism. In the case of antibiosis, some bacterial strains are known to release antibiotics in order to suppress the surrounding bacterial activity, which may be used for biological control of pathogenic species. Likewise, substrate competition is a mechanism that may as well be used to achieve proper biological control, since the bioregulating organism is able to synthesize siderophores microelement quelant agents, which causes microelement deficiency, mainly iron, in the medium, thus inhibiting the respective pathogenic growth (Ongena M. 1998. Conference on biological controls. Training program in the area of biotechnology applied to agriculture and bioindustry. Gembloux, Belgium).

SUMMARY OF THE INVENTION

The invention is related with a composition that contains, at least, one chitinolytic agent or a chitinolytic activity inducing agent, and sulfide or a sulfide producing agent from microorganisms or chemical compounds, where the chitinolytic agent or a chitinolytic activity inducing agent, and sulfide or sulfide producing agent from microorganisms or chemical compounds, are concurrently applied at a substantially minor degree than when each component is used independently to achieve effective control over helminths and causative agents of bacterial and fungal diseases.

The invention is also related with the use of such compositions and/or the concurrent administration of the said compounds from different sources, such as, biologicals and chemicals for effective control over a wide spectrum of plant parasitic nematodes (*Meloidogyne* spp, *Angina* spp, *Ditylenchus* spp, *Pratylenchus* spp, *Heterodera* spp, *Aphelenchus* spp, *Radopholus* spp, *Xiphinema* spp, *Rotylenchulus* spp), animal parasitic nematodes and trematodes (*Haemonchus* spp, *Trichostrongylus* spp, *Dictyocaulus* spp. y *Fasciola hepatica*), bacterial agents causative of diseases (*Erwinia chrysanthemi, Burkholderia glumae*) and fungal agents causative of diseases (*Pestalotia palmarum, Alternaria tabacina, Sarocladium orizae*).

DETAILED DESCRIPTION OF THE INVENTION

The effects of a chitinolytic agent or a chitinolytic activity inducing agent and sulfide, or a sulfide-producing agent on helminths, bacteria and fungi have been previously demonstrated or reported. In this study, however, for the first time, a synergistic effect is demonstrated when both components are concurrently applied.

When the chitinolytic agent, or the chitinolytic activity inducing agent and sulfide or a sulfide producing agent are separately applied, the effects are always less than when the two agents are simultaneously applied.

When applied as a composition of the present invention, the chitinolytic agent or the chitinolytic activity inducing agent and sulfide, or sulfide producing agent can be appropriately mixed in the form of a solution, suspension, emulsion, powder or granulating mixture, and is applied to the plant or soil as a fertilizer, pre-packed soil, covert seed device, a powder, granulate, nebulizer, a suspension, liquid, or any of the indicated form in capsules for the control of parasitic helmiths, and bacterial and fungal diseases.

The optimal application ranges of the chitinolytic agent or the chitinolytic activity inducing agent and sulfide or a sulfide producing agent for the particular case of nematodes, trematodes, bacteria or fungus; and for the case of specific conditions, the ranges are determined through experimental studies, in vitro, greenhouse or under field conditions.

According to the results described in the present invention, a significant control over helminths, bacteria and fungi is achieved with a mixture of 1) a chitinase producing microorganism between $10^7$ Colony Forming Units (CFU) and $10^{12}$ CFU of a particular microorganism per composition gram or chitin between 1% and 50% of the composition; and 2) a sulfide producing microorganism between $10^7$ CFU and $10^{12}$ CFU of a particular microorganism per composition gram, or any sulfide producing chemical agent, where sulfide varies between 1.0 mg/minute per composition gram.

Any composition with a microorganism between $10^7$ CFU and $10^{12}$ CFU per composition gram, that concurrently produces chitinolytic agents and sulfide, is appropriate for the control over helminths, bacteria and fungi. The previous compositions involve combinations of the following agents in the above-mentioned proportions:

1. Chitinase and $Na_2S$.
2. Chitinase and FeS.
3. Chitinase and microorganism *Desulfovibrio desulfuricans*.
4. Chitinase and $Na_2S$.
5. Chitinase and FeS.
6. Chitine and microorganism *Desulfovibrio desulfuricans*.
7. Microorganism that produces chitinolytic activity and $H_2S$ concurrently.

The previous compositions are effective against a wide range of plant parasitic nematodes, including, not limiting *Meloidogyne* species, such as, *M. incognita; Angina* species, such as *A. tritici; Ditylencus* species, such as *D. dipsaci; Pratylenchus* species, such as *P. coffee; Heterodera* species, such as *H. glycines; Aphelenchus* species, such as *A. avenae; Radopholus* species, such as *R. similis; Xiphinema* species, such as *X. index; Rotylenchulus* species, such as *R. reniformis*; zoonematodes such as: *Haemonchus* spp, *Trichostrongylus* spp, *Ostertagia* spp, *Nematodirus* spp, *Cooperia* spp, *Ascaris* spp, *Bunostomum* spp, *Oesophagostomum* spp, *Chabertia* spp, *Trichuris* spp, *Strongylus* spp, *Trichonema* spp., *Dictyocaulus* spp., *Capillaria* spp., *Heterakis* spp., *Toxocara* spp, *Ascaridia* spp, *Oxyuris* spp, *Ancylostoma* spp, *Uncinaria* spp, *Toxascaris* spp and *Parascaris* spp; trematodes, such as *Fasciola hepatica*; plant pathogenic bacteria, such as *Erwinia chrysanthemi, Burkholderia glumae*, and plant pathogenic fungi such as *Pestalotia palmarum, Alternaria tabacina* and *Sarocladium orizae*.

EXAMPLES

Example 1

In Vitro Evaluation of the Nematicidal Effect of Hydrogen Sulfide from Chemical Sources and a Chitinolytic Enzyme Eggs from zoonematodes *Haemonchus* spp and *Trichostrongylus colubriformis* and *Dictyocaulus viviparus* were used, as well as parasitic phytonematode larvae (juveniles 2) from *Melodoigyne incognita*.

Collections of *Haemonchus* spp and *Trichostrongylus colubriformis* nematodes were made from ovine (sheep) and bovine (cattle) abomasa, respectively. The adult female nematodes were washed in a physiological solution and treated with "Hibitane" (Chlorhexidine Acetate) at 0.5%, for 1 minute, the process developed at 37° C. Approximately 100 previously disinfected individuals were introduced into an Erlenmeyer containing 50 ml of LB medium solution, diluted 10 times in distilled sterile water, and were left laying their eggs overnight (8-10 hours).

Collections of *D. viviparous* nematode were made from the infested lung of a bovine (cattle), previously sacrificed. The same procedure was used for *Haemochus* spp. and *T. colubriformis*; however, the females were allowed to lay their eggs for 2-3 hours.

From that moment on, manipulation was done under aseptic conditions in a vertical laminar flow, using 24-well tissue culture plates. The total volume of the medium that contained the females and the eggs was filtered with a sift net of 60 μm. The nematode eggs were trapped on the 30 μm net of a second sifts. It was introduced into a Hibitane solution at 0.5% for 3 minutes, followed by three washes with LB medium diluted 10 times in sterile distilled water.

Once disinfected, the eggs were removed from the sift and were carefully resuspended with a LB medium solution diluted 10 times in sterile distilled water. The final result of the distribution was checked by counting and registering the eggs in each well with an inverted Olympus microscope, observations of the uniformity of the evolutionary state in this phase were made too.

The *Haemonchus* spp and *T. colubriformis'* eggs hatch between 24 and 48 hours of incubation at 28° C., whereas the *D. vivparus'* eggs hatch before 24 hours. A good sample preparation is accomplished when in all the untreated controls more than 60% of hatching occurs in the previously foreseen times for each species.

The collection of egg mass of *Meloidogyne incognita* was performed from squash roots (*Cucurbita pepo*), previously infested and cultivated in greenhouses. For this operation a stereoscope microscope and needles with properly altered tips were used. The masses were put in sterile distilled water in Petri dishes at 28° C., in a number of 50 masses per dish. Daily observations were made to check egg hatching. In approximately 72 hours, there were enough larvae to start collecting and disinfecting.

The total volume of water containing the egg masses and the larvae were filtered through a sift net of 60 μm. From that moment on all the manipulation was done under aseptic conditions in a vertical laminar flow, using 24-well tissue culture plates. The eggs detached from the mass were unable to hatch and remained on the sift net of 30 μm; the larvae were collected with a further net of 5 μm. It was introduced into a Hibitane solution at 0.5% for 3 minutes followed by 3 washes with LB medium diluted 10 times in sterile distilled water. Once disinfected, the *Meloidogyne incognita* larvae were removed from the sift net and carefully resuspended with a LB medium solution diluted 10 times in sterile distilled water. The final collecting and disinfecting results were checked by counting and registering the live larvae with an inverted Olympus microscope.

The nematode's eggs and larvae were placed in a number of 100 individuals in approximately 2 ml of LB medium diluted 10 times. This volume was introduced into safety valves that allow the air to go through the liquid and, therefore, the gasses make contact with the eggs and larvae. Every valve was a replica for each treatment.

The hydrogen sulfide was obtained by a reaction against the chloride acid of two sulfide salts ($Na_2S$ and $FeS$), and from an anaerobial fermentation of bacterium *Desulfovibrio desulfuricans* subs. *desulfuricans* ATCC 27774 (isolated from an ovine rumen). The chitinolytic enzyme used was chitinase SIGMA C 1650, from bacterium *Serratia marcescens*.

The nematode's eggs and larvae under the study were subjected to the following treatments for 24 hours:

1. Control treatment: chitinase not applied, and air circulated through the valve.
2. Chitinase treatment: chitinase at a rate of 0.2 units per replica.
3. Sulfide treatment: hydrogen sulfide from $Na_2S$ with a 0.2 flux at 0.3 mg/minute.
4. Sulfide treatment: hydrogen sulfide from FeS with a 0.2 flux at 0.3 mg/minute.
5. Sulfide treatment: hydrogen sulfide from *Desulfovibrio desulfuricans* with a 0.2 flux at 0.3 mg/minute.
6. Combined treatment: simultaneous application of treatments 2 and 3.
7. Combined treatment: simultaneous application of treatments 2 and 4.
8. Combined treatment: simultaneous application of treatments 2 and 5.

All the above treatments had 4 replicas.

Twenty-four hours after starting the experiment the emerging larvae (*Haemonchus* sp., *T. colubriformis* and *D. viviparous*) and the number of live larvae (*Melodogyne incognita*) in all the treatments, were counted. The effectiveness results (E) are shown in table 1. This value is the mean of the 4 replicas in every treatment. The variance analysis (ANOVA) was applied to the results obtained in each nematode species in the study, separately; the Duncan test (Lerch G. 1977. La Experimentación en las ciencias biológicas y agrícolas. 1$^{ra}$ edición, p.p. 203-308, Editorial Científico-Técnica, La Habana) was applied, which is also shown in table 1. Equal letters indicate that there are no significant differences (p<0.05) among the treatments.

TABLE 1

| | Treatment effectiveness (E)* | | | | | | | |
|---|---|---|---|---|---|---|---|---|
| | Treatment effectiveness (E)* | | | | | | | |
| | 1. Ec Control | 2. Eq | 3. Esn | 4. Esf | 5. Esd | 6. Eqsn (2 + 3) | 7. Eqsf (2 + 4) | 8. Eqsd (2 + 5) |
| *Haemonchus* | 0.00 (a) | 0.32 (b) | 0.41 (c) | 0.40 (c) | 0.37 (b, c) | 0.86 (d) | 0.85 (d) | 0.82 (d) |
| *Trichostrongilus* | 0.00 ($a_1$) | 0.37 ($b_1$) | 0.40 ($b_1, c_1$) | 0.39 ($b_1, c_1$) | 0.38 ($b_1, c_1$) | 0.88 ($d_1$) | 0.88 ($d_1$) | 0.83 ($d_1$) |
| *Dictyocaulus* | 0.00 ($a_2$) | 0.35 ($b_2$) | 0.44 ($c_2$) | 0.42 ($c_2$) | 0.40 ($b_2, c_2$) | 0.91 ($d_2$) | 0.90 ($d_2$) | 0.86 ($d_2$) |
| *Meloidogyne* | 0.00 ($a_3$) | 0.39 ($b_3$) | 0.51 ($c_3$) | 0.52 ($c_3$) | 0.47 ($c_3$) | 0.95 ($d_3$) | 0.93 ($d_3$) | 0.90 ($d_3$) |

*Effectiveness (E) is the result from subtracting the value of active frequency (Fr) for hatching or the live larvae from 1, regarding the case. Fr is the ratio between the number of emerging or live larvae in each treatment (Ntto) and the number of emerging or live larvae in treatment 1 (Nc): E = 1 − Fr, where Fr = Ntto ÷ Nc; therefore, E = 1 − Ntto/Nc To determine the synergic effect in treatments 6, 7 and 8, it was assumed that the events occurring in them are not excluding.

For this type of analysis, the expected effectiveness (EE) must be equal to the sum of the individual effects (EI), given by the effectiveness rendered to the chitinase action (Eq) and the effectiveness rendered to the hydrogen sulfide action (Esn, Esf and Esd), minus the intersection effect (ei) (Sigarroa, A. 1985. Biometría y diseño experimental. 1ra. Parte. Minist. Educación Sup. Ed. Pueblo y EducaciFón. Cap. 3. pag 69-107).

$$EE=Eq+Es-ei, \text{ where } ei=Eq \times Es$$

If the experimental effectiveness (E) in the treatments where two nematicidal agents combine (treatments 6, 7, 8) is greater than the expected effectiveness (EE) for those treatments, it can be assured that there is synergism in terms of the nematicidal activity of the chitinolytic agent (chitinase) and the hydrogen sulfide when both are concurrently applied in the same treatment. The values obtained are summarized in table 2.

TABLE 2

Experimental (E) and expected (EE) effectiveness.

|  | Tratamiento 6 | | Tratamiento 7 | | Tratamiento 8 | |
| --- | --- | --- | --- | --- | --- | --- |
|  | E | EE | E | EE | E | EE |
| Haemonchus | 0.86 | 0.60 | 0.85 | 0.59 | 0.82 | 0.57 |
| Trichostrongilus | 0.88 | 0.62 | 0.88 | 0.62 | 0.83 | 0.61 |
| Dictyocaulus | 0.91 | 0.64 | 0.90 | 0.62 | 0.86 | 0.61 |
| Meloidogyne | 0.95 | 0.70 | 0.93 | 0.71 | 0.90 | 0.68 |

In the three treatments where chitinase and hydrogen sulfide are simultaneously combined, the experimental effectiveness (E) was greater than the expected effectiveness (EE) for the four nematodes under the study, which statistically demonstrates the existence of synergism between both compounds (when they act concurrently), regarding their nematicidal activity. No significant differences were observed as to the origin of the sulfides and their nematicidal effect (TABLE1).

Example 2

Greenhouse Evaluation of the Nematicidal Effect of a Chitinolytic-Activity Inducing Agent (Chitin) and a Hydrogen Sulfide-Producing Agent (*Desulfovibrio desulfuricans* subps. *desulfuricans* ATCC 29577 Isolated from the Soil)

Brown soil with neutral pH was selected: it was dried and sieved with a 0.5 cm net to remove the undesirable particles. It was sterilized in a vertical autoclave for 1 hour at 120° C. and 1 atmosphere (Sambrook J., Fritsch E. F. and Maniatis T. 1989. Molecular Cloning: A Laboratory Manual. $2^{nd}$. Ed. Cold Spring Harbor Laboratory, Cold Spring Harbor, N.Y., USA). It was dried at room temperature for 3-4 days to later make the foreseen mixtures in the treatments with river sand, soil worm humus and chitin (ICN catalogue number 101334).

Twenty pots (15 cm diameter×13 cm depth and 1 liter of capacity) were filled with the set proportions in the following treatments:

1. Control treatment: soil 70%, river sand 25% and humus 5%.
2. Chitin treatment: soil 70%, river sand 25%, humus 4% and chitin 1%.
3. Microorganic treatment: soil 70%, river sand 25%, humus 5% and *D. desulfuricans*, applied to a concentration of $10^{10}$ CFU-pot.
4. Combined treatment: soil 70%, river sand 25%, humus 4%, chitin 1% and *D. desulfuricans* applied to a concentration of $10^{10}$ CFU/pot.

Each treatment was carried out with 5 replicas (pots).

In treatments 2 and 4 a pre-mixture of humus with chitin was made in a 4:1 proportion, followed by a final mixture with the soil and the sand. In treatments 3 and 4, *D. desulfuricans* was applied with 100 ml of de-ionized water per pot. These volumes were uniformly applied during the first irrigation.

For all the treatments, 500 nematode specimens of *Radopholus similis* previously collected from naturally infested banana roots were inoculated in the pots. The centrifugation-floatation technique (Jenkins, W. R. 1964. A rapid centrifugal-flotation technique for separation nematodes from soil. Plant Disease Reporter, 48: 692) was used; the specimens were diluted in 5 ml of distilled water and uniformly applied at a depth of 5 cm under the soil surface.

The pots were placed in greenhouses and remained still for three days after applying the treatments and inoculating the nematodes. Daily irrigation was performed during this stage, in order to preserve the good moisture conditions. Before the fourth day of treatments, a banana plant var. *Cavendish*, achieved by in vitro tissue culture, was transplanted to the pots. From that moment on a strict irrigation regime followed, which allowed permanent soil moisture in its field capacity.

The final evaluation was done three months after the experiment was initiated, the plant's roots were carefully removed from the soil. Then the number of specimens (larvae and adults) and live nematodes collected from the plants, were registered, using the centrifugation-floatation technique (Jenkins, W. R. 1964. A rapid centrifugal-flotation technique for separation nematodes from soil. Plant Disease Reporter, 48: 692), and an inverted microscope for the counts. The effectiveness results for the different treatments are shown in table 3. This is the mean value of the 5 replicas for each treatment. The variance analysis was applied to the results achieved (ANOVA), followed by the Duncan test (Lerch G. 1977. La Experimentación en las ciencias biológicas y agrícolas. $1^{ra}$ edición, p.p. 203-308, Editorial Científico-Técnica, La Habana), shown in table 3. Equal letters indicate that that there are no significant differences (p<0.05) among the treatments.

TABLE 3

Treatment effectiveness (E)*

|  | 1. Ec | 2. Eq | 3. Esd | 4. Eqsd |
| --- | --- | --- | --- | --- |
| *Radopholus similis* | 0.00(a) | 0.21(b) | 0.18(b) | 0.48(c) |

*Effectiveness (E) is the result from subtracting the live specimen relative frequency (Fr) value from 1. Fr is the ratio between the number of live specimens in each treatment (Ntto) and the number of live specimens in treatment 1 (Nc): E = 1 − Fr, where Fr = Ntto/Nc, therefore, E = 1 − Ntto/Nc.

To determine the possible synergic effect in treatment 4, it was assumed that the occurring events (nematicidal effect), are not excluding.

Like Example 1, the expected effectiveness (EE) must be equal to the sum of the individual effects (EI), given by the effectiveness rendered to chitin action (Eq) as an inductor of the chitinolytic activity of the microorganisms present in the mixture of soil and humus, and the effectiveness rendered to the action of hydrogen sulfide (Esd) from bacteria *D. desulfuricans*; minus the intersection effect (ei) between the two treatments (Sigarroa, A. 1985. Biometría y diseño experimental. 1ra. Parte. Minist. Educación Sup. Ed. Pueblo y Educación. Cap. 3. pag 69-107)

$$EE=Eq+Es-ei, \text{ where } ei=Eq \times Es$$

If the experimental effectiveness (E) in treatment 4 where the two nematicidal agents are combined, is greater than the expected effectiveness (EE), it can be assured that there is synergism between the chitinolytic activity-inducing agent (chitin) and hydrogen sulfide (from *D. desulfuricans*), where they are concurrently applied in the same treatment. The values obtained are shown in table 4.

TABLE 4

Experimental (E) and expected (EE) effectiveness.

| | Experimental (E) and expected (EE) effectiveness Treatment 4. | |
|---|---|---|
| | E | EE |
| *Radopholus similis* | 0.48 | 0.35 |

In treatment 4 a chitinolytic activity inductor (chitin), and a biological source of hydrogen sulfide (*D. sulfuricans*) are combined. In this case the experimental effectiveness (E) was greater than the expected effectiveness (EE), thus proving the existence of synergism (regarding its nematicidal activity) in the two compounds when they are concurrently applied in the soil.

Example 3

Demonstration of Chitinolytic Activity and Sulfide Production from Bacteria *Corynebacterium paurometabolum* C-924 and *Tsukamurella paurometabola* DSM 20162

Sulfide Production Determination:

In tubes of 100 ml for gas collection, samples from the gas current from fermentation of strains C-924 and DSM 20162 in 5 l bioreactors, were taken. The total culture time was 24 h. The formation of hydrogen sulfide was detected first at the $16^{th}$ h.

The samples were processed in an analogous manner to the $H_2S$ pattern generated. The analysis was performed in the Varian gas chromatograph, following these conditions:

Flame photometric detector with filter sensitive to compounds that contain sulfur.
Hydrogen sulfide pattern: 43.2 ng/ml, by duplicate.
Samples: duplicate for each time when sampling was done.
Injection: 1 ml or µl of head space.
Column: DB-5 (15 m×0.53 mm)
Temperature: 35° C.
Carrier gas: Nitrogen 1.5 ml/min.
Detector: FPD-S
Purge gas: Nitrogen 30 ml/min.

Table 5 shows a summary of the sulfide gases analysis issued by the two strains at different times.

TABLE 5

Sulfide gases analysis

| | | $H_2S$ flux mg/min (Sulfide flux detected) | | | | |
|---|---|---|---|---|---|---|
| Strains | Samples | 16 hours | 18 hours | 20 hours | 22 hours | 24 hours |
| C-924 | 1 | 0.0673 | 0.2208 | 0.4779 | 0.3578 | 0.0672 |
| | 2 | 0.0659 | 0.2160 | 0.4755 | 0.3552 | 0.0680 |

TABLE 5-continued

Sulfide gases analysis

| | | $H_2S$ flux mg/min (Sulfide flux detected) | | | | |
|---|---|---|---|---|---|---|
| Strains | Samples | 16 hours | 18 hours | 20 hours | 22 hours | 24 hours |
| DSM 20162 | 1 | 0.0231 | 0.0416 | 0.1014 | 0.1863 | 0.0009 |
| | 2 | 0.0240 | 0.0422 | 0.1040 | 0.1887 | 0.0097 |

Both strains produce sulfides, but C-924 produces higher flux than strain DSM 20162.

Chitinolytic Activity Determination:

*Corynebacterium paurometabolum* C-924, *Tsukamurella paurometabola* DSM 20162, *Serratia marcescen* ATCC 13880 and *E. coli* ATCC 25922 strains, were used.

The bacterial cultures of the studied strains were grown in LB medium at 28° C. and 100 rpm for 24 hours, followed by centrifugation at 3500 rpm; the supernatants were filtered through two 0.2 µm nets. The filtered product was assayed in plates prepared with a chitin colloidal suspension (0.5%), agarose was added too, up to 0.8%, to achieve the medium gelling and assure porosity to facilitate protein diffusion. After gelling, 5 mm diameter wells were opened, where 100 µl of the filtered supernatant from each bacterial strain was added. Three replicas were used for every plate, and were incubated at 28° C. in the dark.

From the $48^{th}$ hour on, a decrease was observed in the medium turbidity resembling a halo, which demonstrated chitin hydrolysis. In the following table (TABLE 6), the qualitative results from the occurrence of a hydrolysis halo at different incubation times with the supernatant from the culture of the different strains studied, are shown.

TABLE 6

Occurrence of a hydrolysis halo.

| Strains | 24 hours | 48 hours | 72 hours |
|---|---|---|---|
| *S. marcescen.* | Negative | Positive + | Positive +++ |
| *C. paurometabolum* | Negative | Negative | Positive ++ |
| *T. paurometabola.* | Negative | Negative | Positive + |
| *E. coli.* | Negative | Negative | Negative |

+++ refers to the greatest hydrolysis halo observed,
++ refers to an intermediate hydrolysis halo, and
+ refers to the least hydrolysis halo observed.

Both strains (*C. paurometabolum* and *T. paurometabola*) showed the chitin-hydrolysis halo, just like the positive control used (*S. marcescen*), whereas the *E. coli* strain (negative control) did not produce a hydrolysis halo.

Example 4

In Vitro Evaluation of Effects from Sulfides and Chitinases, Produced by Bacteria *Corynebacterium paurometabolum* C-924 and *Tsukamurella paurometabola* DSM 20162, on Parasite *Fasciola hepatica* (Trematode)

Eggs from parasite *Fasciola hepatica* were used. The egg collections were directly made from the infested liver bile of a bovine (cattle), previously sacrificed. The bile content was resuspended in a 3 times higher volume of distilled water and remained still for 2-3 hours at 28° C., to achieve egg precipitation. Then the greatest possible volume of supernatant liquid was removed. The precipitate was filtered through a sift net of 71 μm, where the eggs were trapped.

From that moment on, all the manipulation was done under aseptic conditions in a vertical laminar flow, using 24-well tissue culture plates. The sift with the *F. hepatica* eggs was introduced into a Hibitane solution at 0.5% for 3 minutes, followed by 3 washes with LB medium diluted 10 times in sterile distilled water. Once disinfected, the eggs were removed from the sift and were carefully resuspended with a LB medium solution diluted 10 times in sterile distilled water. The final collecting and disinfecting results were checked by counting and registering the live larvae with an inverted Olympus microscope.

Observations regarding the uniformity of the evolutionary state in this phase, were made as well.

This parasitic trematode's eggs hatch under the previously in vitro set conditions in about 15 days of incubation at 28° C.; a good preparation of the sample was considered when more than 60% of the eggs hatched at the end of the incubation period.

To develop the experiment, the disinfected eggs were placed in a number of 100 individuals approximately, in 1 ml of LB medium diluted 10 times. The volume was uniformly introduced in 20 safety valves that allow the air passage through the liquid; hence, the gases make contact with the eggs. Each valve was a replica (4 per treatment) in all the five treatments.

The *F. hepatica* eggs were exposed to the following treatments during the last 4 days of incubation:

1. Control treatment: Addition of 1 ml of LB medium diluted 10 times to every valve, with no chitinase, and air circulating through it.
2. Addition to each valve of 1 ml of a chitinolytic supernatant without bacterial cells from a culture of $10^{10}$ Colony Forming Units per milliliter (CFU/ml) of *Corynebacterium paurometabolum* C-924.
3. Addition to each valve of 1 ml of a chitinolytic supernatant without bacterial cells, from a $10^{10}$ CFU/ml of *Tsukamurella paurometabola* DSM 20162.
4. The flux of gases from a continuous culture of *Corynebacterium paurometabolum* C-924 at $10^{10}$ CFU/ml, was allowed to go through the valves.
5. The flux of gases from a continuous culture of *Tsukamurella paurometabola* DSM 20162 at $10^{10}$ CFU/ml, was allowed to go through the valves.
6. Combined treatment: simultaneous application of treatments 2 and 4.
7. Simultaneous treatment: simultaneous application of treatments 3 and 5.

On the fourth day following the start of the experiment, the hatched eggs were counted. In the case of *F. hepatica*, it was not possible to count the larvae (miracides) that come out due to the great motility they have; therefore, observations through the microscope are focused on the eggs. The effectiveness results from the different treatments are shown in table 7. This is the mean value for the 4 replicas in each treatment. Equal letters indicate the lack of significant differences (p<0.05) among the treatments.

TABLE 7

| | Treatment effectiveness (E)* | | | | | | |
| --- | --- | --- | --- | --- | --- | --- | --- |
| | 1. E Control | 2. Eq C-924 | 3. Eq DSM20162 | 4. Es C-924 | 5. Es DSM20162 | 6. E (2 + 4) | 7. E (3 + 5) |
| *Fasciola hepatica* | 0.00 (a) | 0.18 (b) | 0.11 (c) | 0.29 (d) | 0.16 (b, c) | 0.52 (e) | 0.28 (d) |

The effectiveness * is the result from subtracting the relative frequency (Fr) of hatching value from 1. Fr is the ratio between the number of hatched eggs in every treatment (Ntto) and the number of eggs hatched in treatment 1 (Nc): E = 1 − Fr, where Fr = Ntto/Nc; therefore, E = 1 − Ntto/Nc To determine the possible synergic effect in treatments 6 and 7, it was assumed that the events (anti-parasitic effect) occurring in them, are not excluding.

For this type of analysis, the expected effectiveness (EE) is given by the effectiveness rendered to the chitinase action (Eq) and the effectiveness rendered to the action of hydrogen sulfide (Esn, Esf and Esd), minus the intersection effect (ei) (Sigarroa, A. 1985. Biometría y diseño experimental. 1ra. Parte. Minist. Educación Sup. Ed. Pueblo y Educación. Cap. 3. pag 69-107).

$$EE = Eq + Es - ei, \text{ where } ei = Eq \times Es$$

If the experimental effectiveness (E) in the treatments where two anti-parasitic agents combine (treatments 6 and 7), is greater than the expected effectiveness for these treatments, it can be assured that there is synergism in terms of the anti-parasitic activity of the chitinolytic agent (chitinase) and hydrogen sulfide when both are concurrently applied in the same treatment. The values obtained are summarized in table 8.

TABLE 8

| | Experimental (E) and Expected (EE) effectiveness. | | | |
| --- | --- | --- | --- | --- |
| | Treatment 6 | | Treatment 7 | |
| | E | EE | E | EE |
| *Fasciola hepatica* | 0.52 | 0.31 | 0.28 | 0.25 |

In the treatments where chitinase and hydrogen sulfide are combined, the experimental effectiveness (E) was greater than the expected effectiveness (EE), which demonstrates the synergism of the two compounds when acting concurrently in terms of their nematicidal activity.

Example 5

In Vitro Effect Evaluation of a Bacterial Strain (*Corynebacterium paurometabolum* C-924) which Produces Hydrogen Sulfide and has Chitinolytic Activity on Several Bacteria and Fungi The following fungus species were used: *Pestalotia palmarum, Alternaria tabacina, Sarocladium orizae, Pitium debaryanum*; and the following bacterial species: *Erwinia* chrysanthemi, Burkholderia glumae, Serratia marcescen ATCC 13880, Bacillus subtilis F 1695 and Escherichia coli ATCC 25922, were used as well.

A) Fungus Assay.

The interaction of Corynebacterium paurometabolum C-924 on fungi was assayed on these fungi: Pestalotia palmarum, Alternaria tabacina, Sarocladium orizae and Pytium debayianum. Strain of Serratia marcescen ATCC 13880 was used as the positive control for fungicidal activity and E. coli strain ATCC 25922 was used as the negative control for fungicidal activity. The bacterial cultures were grown with the usual shaking and temperature conditions for all species in 24 hours. The necessary dilutions were made with absorbance at λ530 nm to assure a cell concentration of $10^9$ cfu/ml.

They were placed in petry dishes containing PDA medium (agar-potato-dextrose), the inocula were made with a central line and the aid of the microbiological loop. The dishes were incubated for 48 hours at 28° C., then the 8 mm diameter discs from the different fungal strains previously grown were inoculated (plates containing PDA medium) and placed on the plate's surface at either pole regarding the central line of the inoculated bacteria. Three replicas were used for each fungus to be studied and were incubated for 10 days at 28° C. The results were read from the fifth day of the beginning of the experiment on.

b) Bacterium Assay.

The incidence of the interaction of Corynebacterium paurometabolum C-924, E. coli ATCC 25922 and Bacillus subtilis F 1695 was studied in these bacteria: Erwinia chrysanthanem and Burkholderia glumae. The Bacillus subtilis strain F 1695 was used as the positive control for antagonism with other bacteria, for the negative control E. coli strain ATCC 25922 was used. The bacterial strains were grown in LB medium under the usual shaking and temperature conditions for 24 hours. From these cultures, the necessary dilutions were made, with a previous absorbance reading at λ530 nm to assure a cell concentration of $10^9$ cfu/ml. In the case of C-924, drops of 5 μl were applied on three different sites on plates with LB medium, on two different sites for the positive control and two other different sites for the negative control, respectively. The plates were incubated at 28° C. for 48 hours. After that time they were treated with chloroform steam for 3 minutes (to inactivate and avoid dispersion in further steps), then the plates were left in the laminar flow, half-open, to eliminate the gas excess. Inoculation of the challenging strains Erwinia chrysanthemi and Burkholderia glumae, was carried out, which started with pure cultures from every microorganism from which the necessary amounts to make a cellular concentration of $10^9$ cfu/ml were taken, after adding up to three milliliters of semi-solid LB medium (0.1% technical agar No. 3) The mixture was dispersed on the plates containing the challenged strains, then they were incubated at 28° C. for 48 hours to evaluate the results.

Table 9 shows the description of the results accomplished during the above mentioned interaction assays.

TABLE 9

Results accomplished during interaction assays.

| Species | Description | Antagonistic effect of strain C-924. |
|---|---|---|
| Pestalotia palmarum | Fungus, Deuteromiceto, phytopathogenic of foliage and fruits. | +++ |
| Alternaria tabacina | Fungus, Deuteromiceto, phytopathogenic of tobacco leaves. | +++ |
| Sarocladium orizae | Fungus, Deuteromiceto, phytopathogenic of rice, it is involved in the acarus-fungus complex, affecting seeds, sheath and neck. | ++ |
| Pytium debaryanum | Fungus, Oomiceto, lives on the soil and is part of the causative Damping-off complex. | + |
| Erwinia chrysanthemi | Bacterium, isolation of Dahlia stems with soft rottenness symptoms. | +++ |
| Burkholderia glumae | Bacterium, isolation of rice plants with apical and marginal necrosis. | ++ |
| Bacillus subtilis cepa F1695 | Bacterium, isolation of potato rhyzosphere in rottenness-free on affected field. Biorregulator. | − |

+++: Strong antagonism is observed when growth stops and causes the formation of a halo by the effect of C-924. In the case of fungi the typical radial growth is inhibited.
++: Mean antagonist effect of C-924 on the microorganism.
+: Slight antagonist effect of C-924 on the microorganism.
−: No antagonist effect of C-924 is observed on the microorganism.

As shown in table 9, there is a marked antagonist effect of strain Corynebacterium paurometabolum C-924 on fungi Pestlotioa palmarum, Alternaria tabacina and Sarocladium orizae, which are characterized by having a high chitin content in their structures. Only a slight antagonism caused by the action of hydrogen sulfide was observed. In the case of the interaction with the bacteria studied, the antagonism was observed in the two pathogenic strains (Erwinia crhysanthemi and Burkholderia glumae), whereas antagonism was not observed in the case of Bacillus subtilis, as it is isolated from an antagonist soil with other microorganisms and; therefore, more resistant to adverse environmental factors.

What is claimed is:

1. A method for decreasing nematodes in a plant, animal or in soil comprising simultaneously administering and/or applying synergistic amounts of chitinase and hydrogen sulfide in a suitable carrier to the plant, animal or soil, wherein the chitinase is administered in an amount of 0.01 units per milliliter; wherein the hydrogen sulfide is produced by a microorganism with a flux of 0.2 to 0.3 mg/minute; wherein the hydrogen sulfide is obtained from a culture containing between $10^7$ colony forming units (CFU) and $10^{12}$ CFU of microorganisms per milliliter, and wherein the chitinase and hydrogen sulfide are applied simultaneously for a 24 hour period of time.

2. A method according to claim 1, wherein the chitinase is produced by a microorganism.

3. A method according to claim 1, wherein the microorganism is *Corynebacterium paurometabolum*.

4. A method according to claim 1, wherein the hydrogen sulfide and chitinase are applied to the plant or soil as a fertilizer, as a coating seed device, a powder or a granulate.

5. A method according to claim 1, wherein the hydrogen sulfide and chitinase are administered to the animal as a powder, via a nebulizer, as a suspension, or in a capsule.

* * * * *